(12) United States Patent
Noras

(10) Patent No.: US 9,262,942 B2
(45) Date of Patent: Feb. 16, 2016

(54) MRI TRAINING DEVICE

(76) Inventor: Hubert Noras, Wurzburg (DE)

( * ) Notice: Subject to any disclaimer, the term of this patent is extended or adjusted under 35 U.S.C. 154(b) by 215 days.

(21) Appl. No.: 13/584,000

(22) PCT Filed: Mar. 11, 2010

(86) PCT No.: PCT/DE2010/000262
§ 371 (c)(1),
(2), (4) Date: Oct. 16, 2012

(87) PCT Pub. No.: WO2011/110139
PCT Pub. Date: Sep. 15, 2011

(65) Prior Publication Data
US 2013/0045469 A1    Feb. 21, 2013

(51) Int. Cl.
| G01R 33/58 | (2006.01) |
| G09B 23/28 | (2006.01) |
| A61B 5/06 | (2006.01) |
| A61B 17/00 | (2006.01) |
| A61B 19/00 | (2006.01) |

(52) U.S. Cl.
CPC .............. G09B 23/285 (2013.01); A61B 5/061 (2013.01); G01R 33/58 (2013.01); A61B 2017/00725 (2013.01); A61B 2019/5236 (2013.01)

(58) Field of Classification Search
CPC ...................... G09B 23/286; A61N 2005/1091
USPC .......... 5/601; 250/363.04; 324/321; 382/128; 378/65; 424/1.29; 600/410, 567, 411; 623/1.16; 434/262, 265, 267
See application file for complete search history.

(56) References Cited

U.S. PATENT DOCUMENTS

| 4,719,406 A | * | 1/1988 | Schaefer et al. | ............... 324/318 |
| 4,888,555 A | * | 12/1989 | Vaughan et al. | ............... 324/318 |
| 5,285,787 A | * | 2/1994 | Machida | ........................ 600/417 |
| 5,513,992 A | * | 5/1996 | Refait | ........................... 434/267 |
| 5,545,995 A | * | 8/1996 | Schneider et al. | ............. 324/318 |
| 6,544,041 B1 | * | 4/2003 | Damadian | ..................... 434/262 |
| 8,643,369 B2 | * | 2/2014 | Krzyzak | ........................ 324/318 |

(Continued)

FOREIGN PATENT DOCUMENTS

| DE | 10 2005 050 839 B3 | 4/2007 |
| EP | 0640842 A1 | 3/1995 |

(Continued)

OTHER PUBLICATIONS

International Search Report (with English translation) for PCT Application No. PCT/DE2010/000262, dated Nov. 5, 2010, 6 pages.

*Primary Examiner* — Robert J Utama
(74) *Attorney, Agent, or Firm* — Edwin D. Schindler

(57) ABSTRACT

MRI training and adjustment device for positioning the tip of a medical implement in living tissue, comprising a dummy which contains in the space inside it target pieces that show up in the MRI and the other component parts of which are invisible in the MRI, wherein a further component part of the training device is a base plate, which can be fastened under an MRI coil for the living tissue to be examined and carries at least one fastening block, which can be moved linearly with respect to the tissue and to which there can be detachably fastened either the dummy and/or a tissue pressing frame, which has an opening that is crossed by at least one elongated pressing rail, wherein the base plate, the fastening block, the tissue pressing frame and the pressing rail are invisible in the MRI.

11 Claims, 3 Drawing Sheets

(56) References Cited

U.S. PATENT DOCUMENTS

Figure 1:
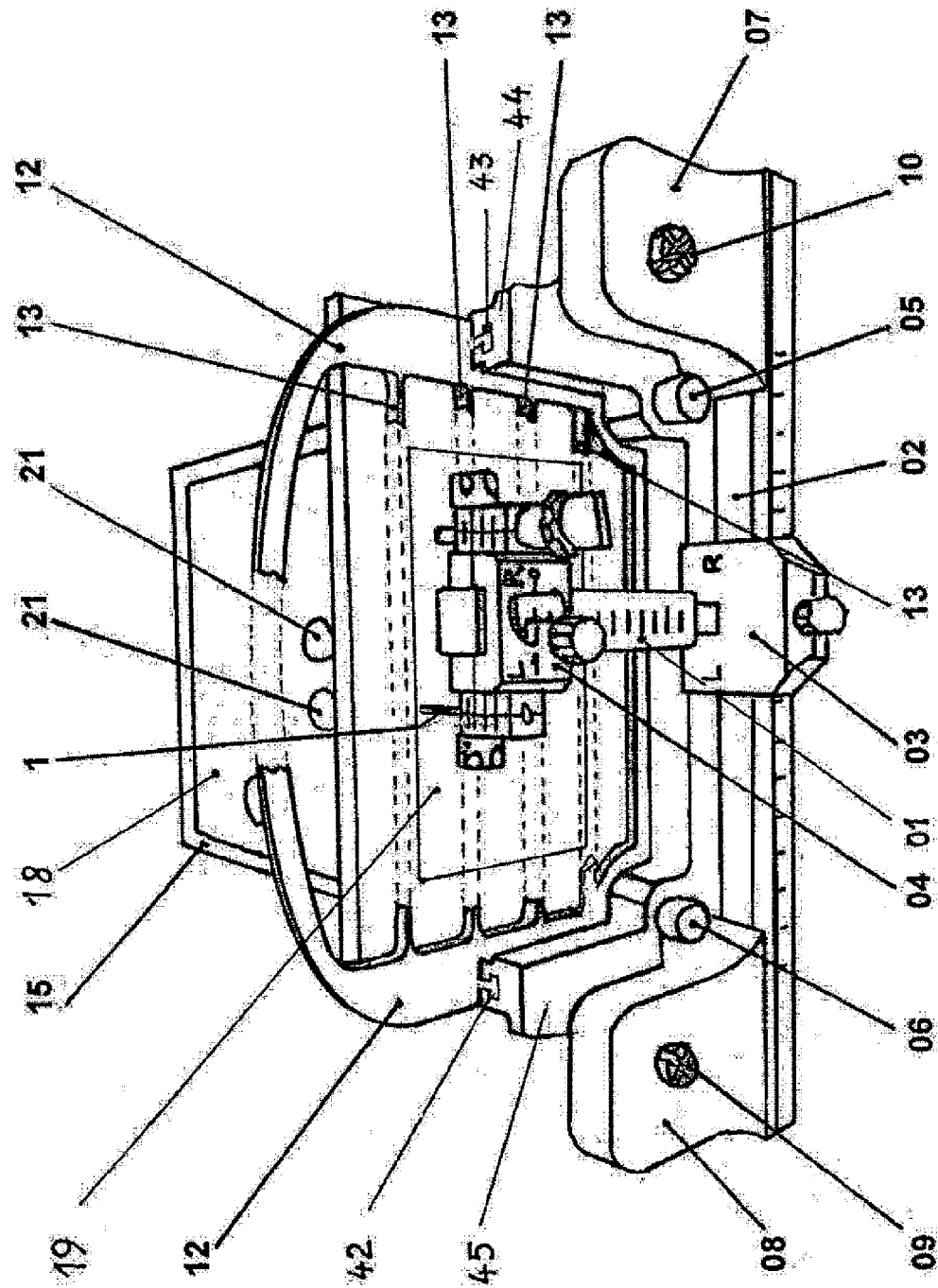

| | | | |
|---|---|---|---|
| 2002/0156365 A1* | 10/2002 | Tsekos | 600/411 |
| 2003/0055436 A1* | 3/2003 | Daum et al. | 606/130 |
| 2004/0102691 A1* | 5/2004 | Mallozzi et al. | 600/410 |
| 2005/0080333 A1 | 4/2005 | Piron et al. | |
| 2007/0016003 A1 | 1/2007 | Piron et al. | |
| 2011/0306025 A1* | 12/2011 | Sheehan et al. | 434/267 |
| 2012/0068699 A1* | 3/2012 | Horkay et al. | 324/300 |
| 2012/0201438 A1* | 8/2012 | Vermandel et al. | 382/128 |
| 2012/0321040 A1* | 12/2012 | Maltbie et al. | 378/62 |

FOREIGN PATENT DOCUMENTS

| | | | | |
|---|---|---|---|---|
| WO | 2008021720 A2 | | 2/2008 | |
| WO | WO 2008021720 A2 * | | 2/2008 | G09B 23/30 |

\* cited by examiner

MRI TRAINING DEVICE

CROSS-REFERENCE TO RELATED APPLICATION

This Application is a Section 371 National Stage Application of International Application No. PCT/ DE2010/000262, filed Mar. 11, 2010 and published as WO 2011/110139 A1 on Sep. 15, 2011, in German, the contents of which are hereby incorporated by reference in their entirety.

MRI training and adjustment device for positioning the tip of a medical implement in living tissue, comprising a phantom which, in the space within it, contains target bodies that show up in the MRI and the other component parts of which are invisible in the MRI.

X-ray devices have been known in principle for about a century as an imaging method for a non-invasive investigation of the body interior of living organism. Because of their radioactive burden, ultrasound-assisted imaging processes were introduced about three decades ago. The latest process is magnetic resonance tomography, also known as nuclear spin tomography, nuclear magnetic resonance (NMR) tomography or magnetic-resonance imaging (MRI). Like the ultrasound process, it does not damage the living organism, but on the contrary can also image bone and is therefore also suitable for complete and large-area tomography of the entire body.

The body to be investigated is moved into a strong and homogeneous static magnetic field—the principal magnetic field—as a result of which the nuclear spin of atomic nuclei, in particular of hydrogen atom nuclei (protons) bound to water, are oriented in the body. High-frequency excitation pulses excite these nuclei to a "precession movement." After the decay of such a high-frequency excitation pulse, the atomic nuclei "precess" with the so-called "Larmor frequency" dependent on the strength of the principal magnetic field and after a tissue-dependent relaxation time, oscillate back to the preferred direction, which is determined by the principal magnetic field.

For each body layer, an image can be generated by computational and measurement analysis of the integral, high frequency nuclear signals from the distribution of the spatial spin density in conjunction with the relaxation times. The nuclear resonance signal that is detectable as a result of the precession movement can be assigned to its point of origin by the application of linear field gradients. To this end, gradient fields corresponding to the principal magnetic field are superimposed and controlled such that the nuclei are only excited in a layer to be imaged. Both for HF excitation of the nuclear spin and for detection of the response signal of the nuclei, an HF coil is necessary.

For example, a breast coil can be placed around a female breast, which hangs down when the patient is lying on her stomach Then, anomalies in the tissues, such as cancerous tumors can be identified while they are still very small.

With the MRI device, it can be diagnosed whether anomalies are present and at what position they are located. The MRI device permits this diagnosis without any injury of the patient—which is a very important advantage. If, however, anomalies have been recognized, physical access at that point is necessary.

To assess whether they are cancerous tumors or other anomalies, it is a very reliable method to remove tiny tissue samples (biopsy) which are then studied in the laboratory. Or medication must be injected as precisely as possible at the location of the anomaly; that is to say the tip of a medical implement—such as a hollow needle—must also be placed at the location of the detected anomaly.

The insertion of this implement, however, within the MRI device is practically impossible. Firstly, the large coil of the principal magnetic field makes mechanical access difficult and secondly because of the particularly strong mechanical field magnetizable materials, such as steel, cannot be used.

Therefore, for the examination and/or treatment, the patient must be moved out of the MRI device and the medical implement must be positioned using the positioning data just determined. To train for this process and also to adjust the device therefor, so-called "phantoms" are known. They are objects that are hardly visible, if at all, in the MRI image, and in which particular points are marked by a substance that is quite clearly visible in the MRI device.

Such a phantom is described in the patent DE 10 2005 050 839 B3. It comprises a multiplicity of spherical elements that are visible in MRI and which are distributed in a uniform grid over the entire volume of the phantom. For orientation, a few of these spatial points, which are visible in MRI, are designed differently from the others.

Such a phantom is suitable for the correction of not entirely correctly computed position data of the MRI device at every point of the space. By virtue of the large number of target points that are visible in MRI, it is however hardly possible at all, therewith, to train how to insert a medical implement with its tip precisely into a particular spatial point, because the route there is blocked by a multiplicity of other spheres in the space.

The essential disadvantage of this phantom, however, is that the user is not assisted in how to arrange and fasten the phantom in the MRI device and how it is ensured that, after the phantom has been moved out of the principal magnetic field coil, the phantom is positioned so precisely with respect to the medical implement that the position values, determined in the MRI method, of the point to be reached in the phantom can also be reached outside the MRI device.

It is also not described how the introduction of the medical implement, that is to say the insertion of a hollow needle, actually takes place.

Another disadvantage of the above-described phantom is that it does not provide help with planning the insertion location and insertion direction.

Against this background, it is the object of the invention to provide a training and adjustment device for positioning the tip of a medical implement into living tissue, with which it is possible to practice on a phantom outside the MRI device, as a spatial point recorded and measured in the MRI device can be reached precisely and on a shortest possible section with the tip of a medical implement.

With the training device, the correct transfer of the positional data determined by measurement in the MRI device on a virtual image in particular is practiced on an actually existing medical implement. In addition the physician can also train how he will introduce the implement into the tissue rapidly and without mistakes during positioning, that is to say with the least possible distressing of the patient.

As a solution, the invention teaches that a further component of the training facility is a base plate, which can be fastened below an MRI coil for the living tissue to be investigated and bears at least one fastening block, which is displaceable linearly with respect to the tissue and on which the phantom and/or a tissue pressure frame can be detachably fastened, which comprises an opening, which is crossed by at least one elongated pressure bar, the base plate, fastening block, tissue pressure frame and pressure bar being invisible in the MRI.

A significant feature of the invention is thus the connection of a device for mechanical fixing of soft body tissue with a phantom.

This device consists of a tissue pressure frame, which is pressed onto tissue, such as a female breast. This frame is crossed by at least one pressure bar. The opening in the tissue pressure frame is preferably filled uniformly by means of a mesh-like structure comprising a plurality of pressure bars. The entire tissue pressure frame is mounted at at least one fastening block, which is linearly displaceable with respect to the base plate.

The function of the tissue pressure frame is explained with the example of a female breast. To this end, the patient is laid on her stomach such that her breasts hang through one opening in each case, which is surrounded by an MRI coil in each case. Below these MRI coils and at a distance therefrom is fastened the base plate, which supports the tissue pressure frame. It can be linearly displaced with respect to the base plate—e.g. by means of a spindle drive—to the extent that it meets the downwardly hanging breast and compresses it. For this purpose, there is arranged, on that side of the breast opposite the tissue pressure frame, a corresponding counterpart, which is either fixed in location or even displaced counterdirectionally to the tissue pressure frame, so that the tissue pressure frame and its counterpart clamp the breast in a similar way to a vise.

By this means, the breast is brought to a defined shape, in which any anomalies of the tissue are brought into a particular position. The breast is also not "displaced" with respect to the device by virtue of the respiration of the patient. If the device remains on the breast, this position can be reproducibly reached again.

The special feature of the tissue pressure frame is that it permits access by the medical implement to the living tissue across almost the entire surface. To this end, the pressure bars generally have a very narrow profile, which is oriented perpendicular to the surface of the living tissue and in this manner only blocks a very small portion of the surface.

In practice, the patient is—as mentioned above—placed on her stomach on the examination table of an MRI device, her breasts hanging down through one MRI coil in each case. Still outside the primary field coil, the breasts are compressed somewhat by linear displacement of the tissue pressure frame and thereby brought into a defined position. Then, in the next step, the patient, together with the tissue pressure frame and its fastening device, is moved into the MRI device and the breast is examined.

If, in the process, tissue anomalies are discovered, their position is determined by the MRI deice and brought to the attention of the examining physician. In the next step, the patient is moved out of the MRI device again, so that the physician can reach the breast, which is still compressed between the tissue pressure frame and its counterpart.

In this position, he can introduce his medical implement into the breast so that the tip of the implement reaches the tissue anomaly. There, he can remove, for example, a tissue sample (biopsy) or leave a mark so that the tissue anomaly can be clearly identified for subsequent treatment, such as, for example, an operation. One possibility of the therapy is, by means of the medical implement, to introduce active substances into the vicinity of the anomaly.

To make this procedure as painless and as short as possible for the patient, with the MRI training and adjustment device according to the invention, he can practice thoroughly and the devices can be adjusted for introducing the needles.

To this end, instead of the tissue pressure frame or behind the tissue pressure frame, the so-called "phantom" is firmly mounted in a particular position. Within the phantom, target bodies are contained, which are imaging in the MRI. The other components of the phantom, such as its walls and its filling are only slightly visible, if at all, in the MRI. Then, in the MRI device, the positions of the target bodies are measured and their spatial coordinates are made known. In the next step, the phantom together with its fastening and the baseplate, in precisely the position in which it was measured, is moved out of the MRI device and, in the next step, the acting physician can introduce his implement into the phantom.

In the process, he practices precisely reaching the existing target bodies, solely using the position data made available by the MRI device for this purpose. If the phantom housing and the phantom filling are transparent, he can check the result of his practice by visual inspection.

If, in these exercises, always the same reproducible deviations are produced, a correction value can be derived therefrom, which must be applied to the guidance of the medical implement.

In order not only to practice the correct "targeting" with the implement, but, to provide the physician with a feeling for introducing the implement into human tissue, the invention proposes as embodiment that the phantom is a container, of which the surface facing the opening of the tissue pressure frame comprises a thin, elastic and skin-like membrane, which can be penetrated by the medical implement. It is thereby simulated that the skin generally opposes the implement with a higher resistance than the inner tissue.

On first contact by the medical implement, the membrane will therefore not open immediately but retracta little. Only when the pressure of the implement is so great that the elastic of the skin is exceeded does it tear somewhat, as a result of which an entrance for the medical implement opens up, by means of which it can penetrate into the tissue.

So that, within the phantom, the behavior of the medical implement during penetration into the tissue is reproduced as accurately as possible, the invention proposes that it is filled with a low-viscosity, jelly-like gel or another material that is similar to human tissue in its mechanical properties and its appearance. The greatest proportion of this gel—about 80-93%—consists of water, preservatives, crosslinking agents and antibiotics. The remaining 7-20% comprises substantatine (??). An alternative recipe would be 0.5-3.0 g $NiSO_4 \cdot 6H_2O$ and 3.0-7.0 NaCl in one liter of distilled water.

As an appropriate mechanical embodiment, the invention proposes that two fastening blocks are arranged on the base plate with a spacing from one another, and can be displaced by means of a threaded spindle in each case in the direction of the living tissue and on which the phantom and/or the tissue pressure frame can be fastened.

As a fastening possibility, the invention proposes T-shaped slots, into which correspondingly complementarily shaped counterparts engage, which are integrally formed on the phantom and on the tissue pressure frame. Alternatively, dovetail connections, pins and bores, snap connections or screws are conceivable.

A very suitable combination for practicing and adjusting the device is provided if both the tissue pressure frame and the phantom are fastened on the fastening blocks. Then the user finds precisely the same conditions-as-in-application-to-a-patient.

The combination of tissue pressure frame and phantom is particularly interesting when the removal implement is to be introduced manually and, as orientation, there serves only the respective field in the tissue-frame opening, which is filled with horizontal and vertical pressure bars in the manner of a grid, and the angle of the implement in a horizontal and vertical direction.

But also if the medical implement is guided with a mechanical implement holder, it is appropriate, in addition to the phantom, also to mount the tissue pressure frame in the MRI training device. It can then be checked whether pressure bars are not actually struck by the medical implement.

To allow the tissue pressure frame to be used both for training and adjustment, as well as on the patient, it is proposed that it can be separated from the phantom.

So that the phantom can alternatively be directly connected to the fastening blocks, it is appropriate to form the same fastening devices on its front side as are also present on the front side of the tissue pressure frame. In this case, the tissue pressure frame must also have T-shaped slots on its back side, which receive the complementary counterpart of the phantom.

Alternatively to a manual guidance of the medical implement, the invention also proposes a mechanical implement holder. A suitable device for this is described in German patent DE 196 26 286 C5, which is hereby expressly declared as a part of this application.

In principle, however, an implement holder that is only adjustable in three degrees of freedom is conceivable. For this purpose, a horizontal adjustment with respect to the tissue pressure frame and a vertical adjustment based thereon would be appropriate. Both adjustments could be performed linearly. The third degree of freedom would be the penetration depth of the medical implement in the living tissue. With such an adjustment in only three degrees of freedom, all the points of the working space can be reached.

A problem could occur, however, if the medical implement precisely meets a pressure bar. With only a small requirement on the precision, it could be attempted, by the elasticity of the medical implement and the elasticity of the pressure bar, to push the medical implement indeed past the pressure bar into the living tissue. However, the positioning accuracy would noticeably deteriorate thereby.

To avoid this disadvantage and also achieve a shortest possible distance from the outer skin of the human tissue as far as the target point, the invention proposes a further degree of freedom. For example, by means of at least one pivot axis or, even better, with two pivot axes, it could be chosen from which direction in space the medical implement ought to be pushed into the living tissue.

As another variant of a shortest possible path of the medical implement from the skin as far as the target point in the human tissue, the invention recommends an additional pivot axis, whose geometrical center point lies on the longitudinal axis of the MRI coil.

If, as application example, an approximately hemispherical female breast is considered, in which a tissue anomaly to be investigated lies very close to the surface, then it is appropriate to pivot this large pivot axis, too, so far that the medical implement is pushed into the tissue approximately perpendicularly to the skin surface.

As a very interesting embodiment, the invention proposes an implement holder comprising a plurality of slides and/or pivot devices oriented orthogonally to one another. These slides and/or these pivot devices can either be manually adjusted and or fixed by means of a clamping screw in each case. Alternatively, they can be moved by means of a motor in each case.

Their respective position can be read via a mechanical scale in the immediate vicinity of the track of a slide or via electronic position actual-value encoders, which are connected to the movement mechanism. They can be, for example, integrated into the drive motor or, in the case of a spindle at the other free end, flange-mounted opposite the drive motor.

In a very simple alternative, the drive motors can be activated by simple keys, which in each case only specify a single speed range and a single direction of rotation. It is more convenient to use levers, which can select various velocity stages as far as an infinitely variable specification of the velocity, in a similar way to an accelerator pedal (gas pedal) of a motor vehicle.

In the case of an actuation of the motors of this kind, any position actual-value encoders present must in each case be connected to a position actual-value display. Depending on the units used for these position actual-value displays, the position setpoint value specified by the MRI device can be very rapidly compared with the position actual value actually achieved.

An alternative is to electrically connect both the motors and the position actual-value encoders to an electronic controller. In a very simple case, all the position setpoint values for the respective drive motors are specified, with the exception of the penetration depth. In the first step, the spatial point specified thereby is still approached outside the tissue or outside the phantom. Only when this point has been reached and only the implement still remains to be driven into the tissue, is, in the second step, the drive in each case activated in order to push the implement precisely to the necessary depth.

For the arrangement of the target bodies in the interior space of the phantom, the invention proposes, as a simple and clearly understandable arrangement, a phantom body with a plurality of stair-like steps. In each step, a depression is formed, which receives a target body in each case. In the simple case of a not precisely measured height of the various steps, they serve only for holding a target body in each case.

If the precise distance of the steps from one another is known, then, after the successful location of a first target body, the relative accuracy of the position actual-value acquisition of the MRI device can be checked. If not only the distance of the steps from one another that is to say their "incremental dimension" is known, but also their difference from a reference point of the phantom, even the absolute accuracy of the position actual-value acquisition by the MRI device can be checked.

A further possible use of a so-called "measured phantom" is the training of the exact positioning without the prior—expensive measurement in an MRI device.

As an appropriate process for training the exact locating the anomaly in living tissue found with the MRI, the invention proposes that, in the first step, the base plate, with the phantom fastened thereon, is fastened below an MRI coil. In the second step, the position of the target body contained in the phantom is measured with an MRI device. Then, in the third step, the base plate with the phantom is separated from the MRI coil and the MRI device and, in the fourth step, the medical implement is guided with its tip into a target body based solely on the position data determined in the second step. As a fifth and last step, the result is checked visually in each case through the wall of the phantom and through the gel.

To adjust an implement holder, the invention proposes repeating the first three steps of the method mentioned above. In the fourth step, the tip of the implement is guided into a target body by means of the implement guide under visual control. In the fifth step, the respective reference point and the respective traverse path of all movement axes of the implement holder is acquired and placed in mathematical relationship with those position data that have been determined in the second step using the MRI device. In future investigations, on actually existing, living tissue, the mathematical relationship determined in this manner can be used for converting the position data determined with the MRI device into position setpoint values for the movement axes of the implement holder.

To practice in advance the manual implement guidance for locating an anomaly in living tissue discovered with the MRI on a phantom, the invention recommends a cycle the first four steps of which correspond to the workflow explained above. In the fifth step, the respective quadrant between the closest vertical and horizontal pressure bars of the tissue pressure frame and the setting angle of the implement in two planes are acquired and mathematically related to those position data that have been determined previously in the second step by means of the MRI device. In future investigations, on actually existing, living tissue, the mathematical relationships determined in this way can be appropriately used for converting the position data determined with the MRI device into a correct manual guidance of the medical implement.

Figure 2:
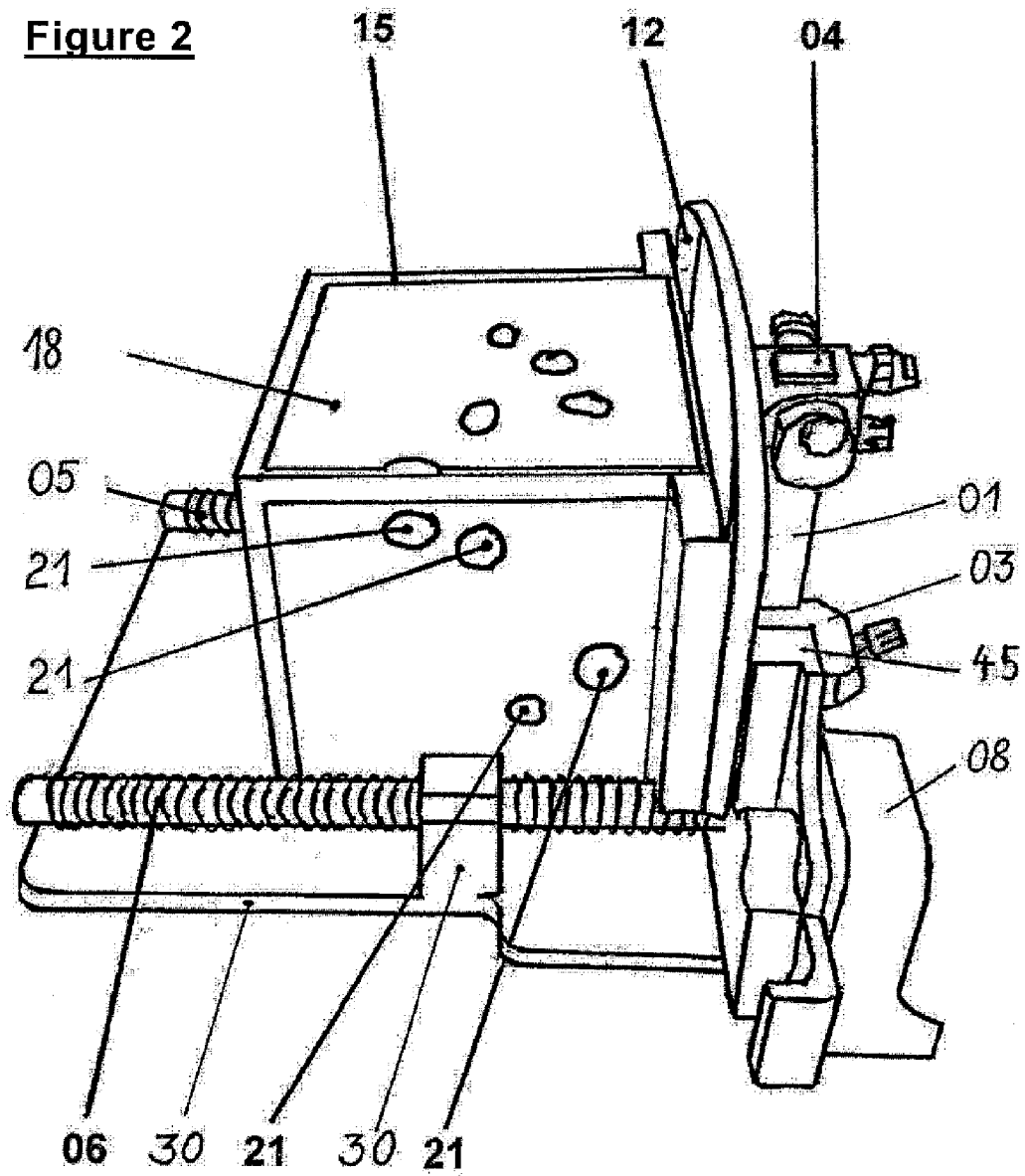
Figure 3:
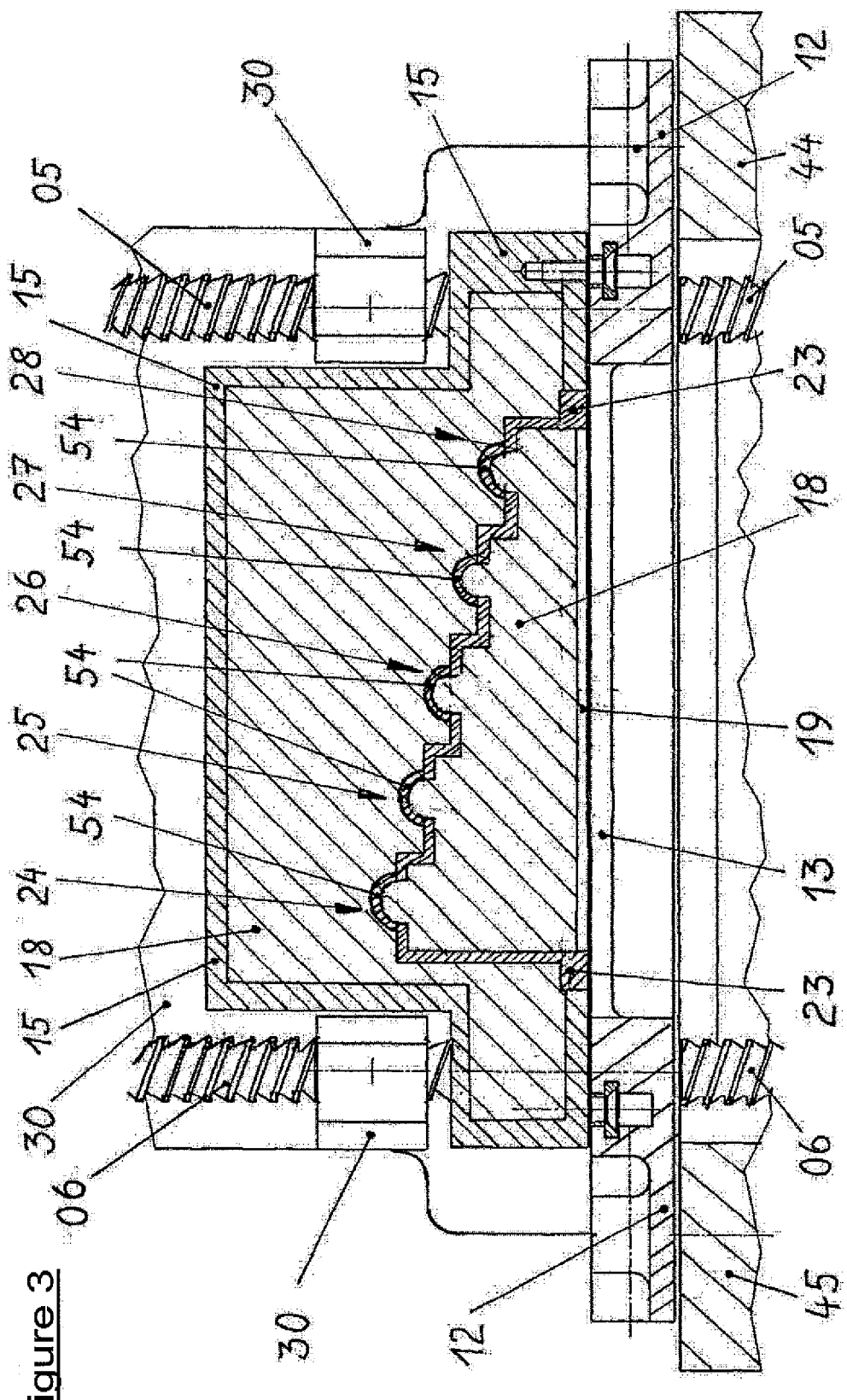

Further details and features of the invention are explained below in greater detail with reference to examples. However, they are not intended to limit the invention but only explain it. In schematic view:

FIG. 1. Shows an oblique view of an MRI training device with device pressure frame and phantom from the implement side FIG. 2 shows the MRI training device as in FIG. 1, but in side view FIG. 3 shows a horizontal section through an MRI training device as FIGS. 1 and 2, but with a different phantom with inserted stair-like phantom body In FIG. 1, the implement side of an MRI training device is shown in perspective view. In the picture center, the tissue pressure frame 12 can be seen, which comprises a large opening, though which a plurality of horizontal pressure bars 13 run, which are for the most part drawn broken and open a view of the phantom 15, which is placed against the back side of the tissue pressure frame 12 instead of human tissue.

In the FIG. it is not shown that, during normal operation of the MRI training device in an MRI device, the phantom 15 is removed and the other, illustrated arrangement is inserted directly below an MRI coil of the MRI device. Then, for example, female breasts hanging through the MRI coil can be brought into a precisely measurable position for a diagnosis of tissue anomalies by moving the pressure frame 12 by means of the two threaded spindles 05 and 06 against the breast until it is in full contact therewith, as a result of which the breast is brought into a precisely defined form and position. To this end, the tissue pressure frame 12 comprises numerous pressure bars 13 in its large opening.

Then, with the MRI device, anomalies such as, for example, cancerous tissues can be sought and the position of discovered tumors can be precisely measured. Such cancerous tumors correspond to the target body 21 in the phantom 15.

The position data of the discovered tumors, or, if appropriate, of the target bodies are read by the MRI device. The tip of the medical implement 1 must then be guided to this point.

In the simplest case—which is not shown in FIG. 1 but is readily understandable—of manual introduction of the medical implement 1 into the living tissue, the pressure bars 13 can also serve as support or at least as orientation aid.

In most cases, the medical implement 1 is a hollow needle, which is pierced into the human tissue. This piercing must be performed outside the MRI device and therefore without any possibility of control. After each piercing, the patient must thus be moved back into the MRI device to check whether the direction and penetration depth of the medical implement 1 are correct.

Since any errors in this positioning accuracy are extremely painful for the patient, the doctor can practice the correct piercing on the MRI training device according to the invention, which is shown in FIG. 1. To this end, the phantom 15 is used instead of human tissue.

In FIG. 1, it can be seen that the phantom 15 contains some small target bodies 21 in its interior. They are surrounded by the gel 18, which is hardly visible, if at all, in the MRI. Likewise, the walls of the phantom 15 are also invisible in the MRI device, so that the MRI device recognizes the target bodies 21 and can measure their position. The walls and the gel 18 are also optically transparent, so that the result of the target search can always be optically controlled.

In FIG. 1, it can also be clearly understood how, by means of the training device, the physician's feeling for the introduction of the medical implement, such as the piercing with a needle-shaped medical implement 1 can be practiced in the phantom 15. For this purpose a membrane 19 is mounted on the front side of the phantom 15. It seals the opening of the phantom 15, which faces the tissue pressure frame 12, and thereby keeps back the gel 18 that is located in the interior of the phantom 15. It can be penetrated by the medical implement 1, but with a considerably higher resistance than the gel 18 In the FIG., it is shown how a medical implement 1 enters the membrane 19. It is not shown that, in the process, the membrane 19 is first deformed somewhat around the implement until it is cut somewhat and the implement 1 enters through the cut. The elastic membrane prevents gel 18 emerging next to the puncture point.

The embodiment in FIG. 1 shows a multiply adjustable implement holder for the medical implement 1. It rests on the implement carrier plate 02, which is fastened at both ends on a web 07 and 08 in each case. These webs 07, 08 are connected via pins 09, 10 to the fastening blocks 44 and 45. These fastening blocks 44, 45 in turn bear the tissue pressure frame 12.

In the illustrated embodiment, a horizontal slide 03 can be displaced to the left (L) and right (R) on the implement carrier plate 02. In FIG. 1, it can be readily seen that the horizontal slide 2 travels along a mark on the front side of the implement carrier plate 02. Its position actual value can be read by means of a scale. The position of the horizontal slide 03 can be fixed by means of the knurled screw that can be seen in the center of the horizontal slide 03.

In a similar way, the vertical slide 01, which performs the movement of the medical implement in a vertical direction, is erected on the horizontal slide 03.

In addition, in the embodiment shown in FIG. 1, the inclination of the medical implement can be changed by means of a pivot axis, which is not shown in detail and is arranged at the right edge of the depth slide 04.

On top of the vertical slide 01, as a further slide, there is positioned the depth slide 04, with which the medical implement 1 can be pushed onto the membrane 19 until the tension of the membrane 19 is so great that it lets the medical implement 1 through. In the further continuation, with relatively low resistance through the gel 18 until it (hopefully) meets with a target body 21.

As a result, the implement holder is always in a clear geometrical relationship to the target bodies 21.

In FIG. 1, it can be very clearly understood that a principal effect of the MRI training device is that, during training, the implement 1 is not inserted into an absolutely opaque body part as in practice on the living tissue, but that, via transparent walls of the phantom 15 and thanks to the transparency of the gel 18, it can also be optically precisely tracked at which point the tip of the medical implement (hollow needle) is currently situated, and what path it still has to cover to successfully locate a target body 21.

In FIG. 1, in the two fastening blocks 44 and 45, it is drawn as a possible alternative embodiment, that they comprise a T-shaped guide 42, 43 in each case, in which a complementary portion on the tissue pressure frame 12 engages in each case. By this means the tissue pressure frame 12 can be inserted from above into the fastening blocks 44 and 45, where it is well secured, even over a relatively long service time.

In FIG. 1, it can be clearly seen that, instead of the tissue pressure frame 12, the phantom 15, too, can be directly connected to the fastening blocks 44, 45, if it also has, on its front side, fastening elements, which can be inserted into the guides 42 and 43.

In FIG. 2, the same arrangement as in FIG. 1 is shown from the side in perspective. It can be readily seen that, in this embodiment, the phantom 15 comprises a rectangular housing, which is formed at its edges by a frame and the surfaces of which are in each case transparent, so that it permits a view of the target bodies 21. The latter are located in a position, which is not closely defined, within the gel 18, which is also transparent and fills the interior of the phantom.

In FIG. 2, it is made clear that the rectangular phantom 15 is fastened with its front on the back side of the tissue pressure frame 12.

FIG. 2 makes it clear that the entire module comprises a phantom 15 and tissue pressure frame 12, and the fastening blocks 44 and 45, and the webs 07 and 08 fastened thereon, together with the implement holder, which is fastened thereon, are fastened via the fastening blocks 44 and 45 at one end of a threaded spindle 05 and 06 in each case. By rotation of the threaded spindles, the entire assembly can be displaced with respect to the base plate 30.

This displacement is not relevant for training operation, but is the crucial functional feature for the use of the MRI training device with the phantom 15 removed. Then, by rotation of the two threaded spindles 05 and 06, the tissue pressure frame is pressed against the living tissue to be investigated.

FIG. 3 shows a horizontal section through the same mechanical arrangement as in FIGS. 1 and 2, but with a somewhat changed phantom 15, which, in its interior, bears a phantom body 23 directly opposite the membrane 19. This phantom body 23 has the stair-like steps 24 to 28, which in the illustrated embodiment are in each case spaced from their two neighbors by the same amount. On each of the five steps 24 to 28, a depression 54 in each case is attached, which is hemispherical in the illustrated embodiment. A target body 21—which is not shown here—is placed therein.

If the precise spacings of the steps 24 to 28 of the membrane 19, and also the other coordinates of the depression 54, are known then, it can be clearly understood in FIG. 3 how, with an MRI training device configured in this manner, even without making use of the expensive prior measurement of the target bodies 21 by means of and MRI device, the accurately targeted insertion of the medical implement can be practiced.

Instead of the position actual-value values from the MRI device, the known positions of the depressions 54 are made use of. The result can be optically controlled in a simple manner.

With a consideration of FIG. 3, it can be readily understood that the depressions 54, which are here shown at the same level in each case, can be arranged at various positions vertically with respect to the sectional plane, which makes the training more interesting and more realistic. In FIG. 3, for the sake of clarity, all five depressions 54 are shown at the same level.

List Of Reference Characters
01 Vertical slide
02 Implement carrier plate
03 Horizontal slide
04 Depth slide
05 Threaded spindle, right or fastening block 44
06 Threaded spindle, left for fastening block 45
07 Web, right, fastened on the fastening block 44 with pins 10
08 Web, left, fastened on the fastening block 45 with pins 9
09, 10 Pins, connecting the webs 07, 08 to the fastening blocks 44, 45
1 Medical implement, reaching through the tissue pressure frame 12 into living tissue or into the phantom 15
12 Tissue pressure frame, can be pressed onto living tissue
13 Pressure bar, in an opening in the tissue pressure frame 12
15 Phantom, can be mounted on the fastening block 44, 45 or on the tissue pressure frame 12 as an alternative to living tissue.
18 Gel in the interior of the phantom 15
19 Membrane, sealing the opening of the phantom 15, which faces the tissue pressure frame 12
21 Target body, visible by MRI
23 Phantom body in the phantom 15
24-28 Stair-like step of the phantom body 23
30 Base plate, bearing fastenings for threaded spindles 05, 06
42 Guide, left, for fastening the phantom 15 or the tissue pressure frame 12
43 Guide, as 42, but right
44 Fastening block, right, bearing phantom 15 or tissue pressure frame 12
45 Fastening block, as 44, but left,
54 Depression in steps 24-28 for target bodies 21

The invention claimed is:

1. A MRI training and adjustment device for simulating positioning a tip of a medical implement in living tissue using an MRI device, comprising:
  a phantom,
    which contains in its interior, viewable target bodies, which are viewable using the MRI device, and non-viewable target bodies, which are not viewable using the MRI device, and
    a base plate,
  at least one fastening block
    a tissue pressure frame attached to the at least one fastening block
  wherein the tissue pressure frame comprises an opening, which is crossed by at least one elongated pressure bar, and wherein
  the base plate, the fastening block, the tissue pressure frame and the elongated pressure bar are invisible to the MRI device.

2. The MRI training device according to claim 1, wherein the phantom is a container, of which that surface facing the opening of the tissue pressure frame comprises an elastic skin-like membrane which is penetrable by the medical implement.

3. The MRI training device according to claim 2, wherein the phantom is filled with a low-viscosity jelly-like gel that resembles human tissue in its mechanical properties.

4. The MRI training device according to claim 1, wherein the at least one fastening blocks comprises two fastening blocks arranged on the base plate and spaced from one another, the two fastening blocks
   are displaceable in the direction of the viewable target bodies.

5. The MRI training device according to claim 1, wherein the base plate bears an implement holder, wherein the implement holder is adjustable in at least three spatial degrees of freedom.

6. The MRI training device according to claim 5, wherein the implement holder is adjustable using a plurality of
   slides that are oriented orthogonally with respect to one another or
   pivot devices.

7. The MRI training device according to claim 1, further comprising stair-like steps in the interior space of the phantom, wherein each of the stair-like steps includes a depression.

8. The MRI training device according to claim 7, wherein each of the depressions is hemispherical.

9. A method for training targeting of an anomaly discovered by means of MRI in living tissue with a medical implement comprising:
   providing a MRI device including a MRI coil;
   providing a MRI training and adjustment device comprising:
      a phantom having target bodies in an interior that are viewable using the MRI device;
      a tissue pressure frame including an opening, which is crossed by at least one elongated pressure bar; and
      a base plate including at least one fastening block that is releasably fastened to at least one of the phantom and the tissue pressure frame;
      wherein the base plate, the fastening block, the tissue pressure frame and the pressure bar are invisible to the MRI device;
   fastening the base plate and the attached phantom beneath the MRI coil;
   measuring a position of a selected target body contained in the phantom including collecting position data using the MRI device;
   separating the base plate and the phantom from the MRI coil and the MRI device;
   guiding a tip of a medical implement into the selected target body based on the position data; and
   visually inspecting the location of the tip of the medical implement through a wall of the phantom.

10. The method according to claim 9, wherein:
   guiding a tip of a medical implement into the selected target body comprises guiding the medical implement using an implement holder under visual control; and
   visually inspecting the location of the tip of the medical implement comprises acquiring a respective reference point and a respective traverse path of all movement axes of the implement holder, and placing in mathematical relationship with the position data.

11. The method according to claim 10, wherein visually inspecting the location of the tip of the medical implement comprises acquiring a respective quadrant between the nearest pressure bars of the pressure frame and a setting angle of the implement holder in two planes, and placing in mathematical relationship with the position data.

* * * * *